United States Patent
Hundorf et al.

(10) Patent No.: US 9,849,040 B2
(45) Date of Patent: *Dec. 26, 2017

(54) METHOD AND APPARATUS FOR MAKING DISPOSABLE ABSORBENT ARTICLE WITH ABSORBENT PARTICULATE POLYMER MATERIAL AND ARTICLE MADE THEREWITH

(71) Applicant: The Procter & Gamble Company, Cincinnati, OH (US)

(72) Inventors: Harald Hermann Hundorf, Bonn (DE); Miguel Brandt Sanz, Tervuren (BE); Holger Beruda, Schwalbach (DE); Horst Blessing, Cincinnati, OH (US); Peter Dziezok, Hochheim (DE); Axel Krause, Erfstadt (DE); Mattias Schmidt, Idstein (DE); Lutz Stelzig, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 250 days.

This patent is subject to a terminal disclaimer.

(21) Appl. No.: 14/549,573

(22) Filed: Nov. 21, 2014

(65) Prior Publication Data

US 2015/0075711 A1    Mar. 19, 2015

Related U.S. Application Data

(60) Continuation of application No. 13/477,131, filed on May 22, 2012, now Pat. No. 8,919,407, which is a
(Continued)

(51) Int. Cl.
 *B32B 37/12*  (2006.01)
 *A61F 13/532* (2006.01)
 (Continued)

(52) U.S. Cl.
 CPC .. *A61F 13/15634* (2013.01); *A61F 13/15658* (2013.01); *A61F 13/15699* (2013.01);
 (Continued)

(58) Field of Classification Search
 CPC ........ B32B 5/16; B32B 5/30; B32B 37/1207; B32B 37/1284; B32B 37/24;
 (Continued)

(56) References Cited

U.S. PATENT DOCUMENTS

| 3,860,003 A | 1/1975 | Buell |
| 4,610,678 A | 9/1986 | Weisman et al. |

(Continued)

FOREIGN PATENT DOCUMENTS

| EP | 0149880 A2 | 7/1985 |
| JP | 07-124193 A | 5/1995 |

(Continued)

*Primary Examiner* — Michael Tolin
(74) *Attorney, Agent, or Firm* — Wednesday G. Shipp

(57) ABSTRACT

A method for making a disposable absorbent core comprises depositing absorbent particulate polymer material from a plurality of reservoirs in a printing roll onto a substrate disposed on a grid of a support which includes a plurality of cross bars extending substantially parallel to and spaced from one another so as to form channels extending between the plurality of cross bars. The plurality of reservoirs in the first peripheral surface are arranged in an array comprising rows extending substantially parallel to and spaced from one another. A disposable absorbent article and apparatus for making an absorbent article are also disclosed.

12 Claims, 13 Drawing Sheets

Related U.S. Application Data division of application No. 12/534,286, filed on Aug. 3, 2009, now Pat. No. 8,206,533.

(60) Provisional application No. 61/091,799, filed on Aug. 26, 2008.

(51) Int. Cl.

| A61F 13/15 | (2006.01) |
|---|---|
| B32B 5/30 | (2006.01) |
| B32B 37/24 | (2006.01) |
| B05C 19/00 | (2006.01) |
| A61F 13/53 | (2006.01) |
| A61F 13/539 | (2006.01) |

(52) U.S. Cl.
CPC .......... *A61F 13/5323* (2013.01); *B05C 19/00* (2013.01); *B32B 5/30* (2013.01); *B32B 37/1207* (2013.01); *B32B 37/1284* (2013.01); *B32B 37/24* (2013.01); *A61F 2013/530496* (2013.01); *A61F 2013/530554* (2013.01); *A61F 2013/530562* (2013.01); *A61F 2013/53958* (2013.01); *Y10T 156/1007* (2015.01)

(58) Field of Classification Search
CPC ........ B32B 2037/1215; B32B 38/1833; B32B 38/1841; B32B 38/1858; B05C 1/08; B05C 1/0808; B05C 19/00; B05C 19/008; A61F 13/15658; A61F 13/15699; A61F 13/5323; A61F 13/535; A61F 13/539; A61F 2013/53051; A61F 2013/530547; A61F 2013/530554; A61F 2013/530562; A61F 2013/530591; A61F 2013/53908; A61F 2013/5395; A61F 2013/53958

See application file for complete search history.

(56) References Cited

U.S. PATENT DOCUMENTS

| 4,834,735 | A | 5/1989 | Alemany et al. |
|---|---|---|---|
| 4,888,231 | A | 12/1989 | Angstadt |
| 4,940,464 | A | 7/1990 | VanGompel et al. |
| 5,037,416 | A | 8/1991 | Allen et al. |
| 5,092,861 | A | 3/1992 | Nomura et al. |
| 5,137,537 | A | 8/1992 | Herron et al. |
| 5,151,092 | A | 9/1992 | Buell et al. |
| 5,246,433 | A | 9/1993 | Hasse et al. |
| 5,260,345 | A | 11/1993 | DesMarais et al. |
| 5,269,775 | A | 12/1993 | Freeland et al. |
| 5,387,207 | A | 2/1995 | Dyer et al. |
| 5,397,316 | A | 3/1995 | LaVon et al. |
| 5,554,145 | A | 9/1996 | Roe et al. |
| 5,569,234 | A | 10/1996 | Buell et al. |
| 5,571,096 | A | 11/1996 | Dobrin et al. |
| 5,650,222 | A | 7/1997 | DesMarais et al. |
| 5,897,545 | A | 4/1999 | Kline et al. |
| 5,957,908 | A | 9/1999 | Kline et al. |
| 6,004,306 | A | 12/1999 | Robles et al. |
| 6,120,487 | A | 9/2000 | Ashton |
| 6,120,489 | A | 9/2000 | Johnson et al. |
| 6,645,569 | B2 | 11/2003 | Cramer et al. |
| 6,837,281 | B2 | 1/2005 | Spiers et al. |
| 6,863,933 | B2 | 3/2005 | Cramer et al. |
| 7,112,621 | B2 | 9/2006 | Rohrbaugh et al. |
| 7,837,662 | B2 | 11/2010 | Nakagawa et al. |
| 8,206,533 | B2 | 6/2012 | Hundorf et al. |
| 2003/0105190 | A1 | 6/2003 | Diehl et al. |
| 2003/0148684 | A1 | 8/2003 | Cramer et al. |
| 2003/0233082 | A1 | 12/2003 | Kline et al. |
| 2004/0158212 | A1 | 8/2004 | Ponomarenko et al. |
| 2004/0162536 | A1 | 8/2004 | Becker et al. |
| 2005/0008839 | A1 | 1/2005 | Cramer et al. |
| 2005/0159720 | A1 | 7/2005 | Gentilcore et al. |
| 2006/0021695 | A1 | 2/2006 | Blessing et al. |
| 2006/0048880 | A1 | 3/2006 | Blessing et al. |
| 2006/0278335 | A1* | 12/2006 | Moriura ............ A61F 13/15658 156/279 |
| 2007/0027435 | A1* | 2/2007 | Nakagawa ........ A61F 13/15203 604/368 |
| 2007/0118087 | A1 | 5/2007 | Flohr et al. |
| 2008/0312617 | A1 | 12/2008 | Hundorf et al. |
| 2008/0312618 | A1 | 12/2008 | Hundorf et al. |
| 2008/0312619 | A1 | 12/2008 | Ashton et al. |
| 2008/0312620 | A1 | 12/2008 | Ashton et al. |
| 2008/0312621 | A1 | 12/2008 | Hundorf et al. |
| 2008/0312622 | A1 | 12/2008 | Hundorf et al. |
| 2008/0312623 | A1 | 12/2008 | Hundorf et al. |
| 2008/0312624 | A1* | 12/2008 | Hundorf ............. A61F 13/5323 604/366 |
| 2008/0312625 | A1 | 12/2008 | Hundorf et al. |
| 2008/0312628 | A1 | 12/2008 | Hundorf et al. |
| 2009/0266478 | A1 | 10/2009 | Schafer et al. |
| 2009/0270825 | A1 | 10/2009 | Wciorka et al. |
| 2010/0004614 | A1 | 1/2010 | Ashton et al. |
| 2010/0051166 | A1 | 3/2010 | Hundorf et al. |
| 2010/0305533 | A1 | 12/2010 | Ashton et al. |
| 2010/0305537 | A1* | 12/2010 | Ashton ............. A61F 13/49001 604/374 |
| 2011/0041999 | A1 | 2/2011 | Hundorf et al. |
| 2011/0288513 | A1 | 11/2011 | Hundorf et al. |
| 2014/0324007 | A1* | 10/2014 | Hundorf ........... A61F 13/15658 604/366 |
| 2014/0324008 | A1* | 10/2014 | Hundorf ............. A61F 13/5323 604/366 |
| 2015/0230999 | A1* | 8/2015 | Wciorka ............... A61F 13/539 604/365 |
| 2016/0095761 | A1* | 4/2016 | Hundorf ............. A61F 13/5323 604/365 |
| 2016/0235606 | A1* | 8/2016 | Ashton ................. A61F 13/532 |

FOREIGN PATENT DOCUMENTS

| JP | 2002-113800 A | 4/2002 |
|---|---|---|
| WO | WO 95/16746 A1 | 6/1995 |
| WO | WO 02/064877 A2 | 8/2002 |
| WO | WO2007/014235 A1 | 2/2007 |

* cited by examiner

METHOD AND APPARATUS FOR MAKING DISPOSABLE ABSORBENT ARTICLE WITH ABSORBENT PARTICULATE POLYMER MATERIAL AND ARTICLE MADE THEREWITH

FIELD OF THE INVENTION

The present invention generally relates to an absorbent article and a method and apparatus for making an absorbent article, and more particularly to a method and apparatus for making a disposable absorbent article with absorbent particulate polymer material, such as a diaper.

BACKGROUND OF THE INVENTION

Absorbent articles, such as disposable diapers, training pants, and adult incontinence undergarments, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Some absorbent articles, like diapers, contain an absorbent polymer material (also known as super absorbent polymer), such as an absorbent particulate polymer material. Absorbent particulate polymer material absorbs liquid and swells and may be more effective when disposed in an absorbent article in a certain pattern or arrangement intended for optimal absorbency, fit, and/or comfort. Thus, it may be desirable for absorbent particulate polymer material to remain in its intended location in an absorbent article and absorbent particulate polymer material, therefore, is desirably immobilized in the absorbent article such that the absorbent particulate polymer material remains immobilized when the absorbent article is dry and when it is wet.

In addition to being absorbent, absorbent articles, such as diapers, may desirably be thin and flexible, for ease and comfort in use and for more convenient and neat packaging and storage. Absorbent articles, which may often be used in large quantities, may also desirably be inexpensive. Some technologies of immobilizing absorbent particulate polymer material in an absorbent article add bulk to the absorbent article and thereby increase thickness, reduce flexibility, and/or increase cost of the absorbent article. Other technologies for immobilizing absorbent particulate polymer material in an absorbent article may not be as effective in maintaining immobilization when the absorbent article is in the wet state as when in the dry state. Accordingly, there remains a need for a thin, flexible, and/or inexpensive absorbent article containing absorbent particulate polymer material with enhanced immobilization of the absorbent particulate polymer material in the article in dry and wet states.

SUMMARY OF THE INVENTION

The present invention addresses one or more technical problems described above and provides a method for making a disposable absorbent article which may comprise depositing absorbent particulate polymer material from a plurality of reservoirs in a printing roll onto a substrate disposed on a grid of a support which includes a plurality of cross bars extending substantially parallel to and spaced from one another so as to form channels extending between the plurality of cross bars. The plurality of reservoirs in the first peripheral surface may be arranged in an array comprising rows extending substantially parallel to and spaced from one another. The support and printing roll may be arranged such that the plurality of cross bars are substantially parallel to the rows of the plurality of reservoirs and the absorbent particulate polymer material is deposited on the substrate in a pattern such that the absorbent particulate polymer material collects in rows on the first substrate formed between the first plurality of cross bars. A thermoplastic adhesive material may be deposited on the absorbent particulate polymer material and the substrate to cover the absorbent particulate polymer material on the substrate and form an absorbent layer.

According to another aspect of this invention, an apparatus for making a disposable absorbent article may comprise an absorbent particulate polymer material feeder, a support comprising a grid, a printing roll, and a thermoplastic adhesive material applicator. The support may comprise a grid including a plurality of cross bars extending substantially parallel to and spaced from one another so as to form channels extending between the plurality of cross bars. The printing roll may be structured for receiving absorbent particulate polymer material from the absorbent particulate polymer material feeder and have a peripheral surface and a plurality of reservoirs in the peripheral surface arranged in an array comprising rows extending substantially parallel to and spaced from one another. The support and printing roll may be arranged such that the plurality of cross bars are substantially parallel to the rows of the plurality of reservoirs in the peripheral surface, so that, when the printing roll rotates, the plurality of reservoirs roll receive absorbent particulate polymer material from the absorbent particulate polymer material feeder and deposit the absorbent particulate polymer material on the substrate in a pattern such that the absorbent particulate polymer material collects in rows on the substrate formed between the plurality of cross bars. The thermoplastic adhesive material applicator may apply thermoplastic adhesive material applicator on the absorbent particulate polymer material and the substrate to cover the absorbent particulate polymer material on the substrate and form an absorbent layer.

According to yet another aspect of this invention, a disposable absorbent article may comprise a chassis, including a topsheet and a backsheet, and a substantially cellulose free absorbent core located between the topsheet and the backsheet. The absorbent core may have a longitudinal axis, and may include first and second absorbent layers. The first absorbent layer may include a first substrate and the second absorbent layer including a second substrate. The first and second absorbent layers may further include absorbent particulate polymer material deposited on the first and second substrates and thermoplastic adhesive material may cover the absorbent particulate polymer material on the respective first and second substrates. The absorbent particulate polymer material may be deposited on the first and second substrates in respective patterns and each pattern may comprise rows of the absorbent particulate polymer material spaced from one another extending substantially perpendicular to the longitudinal axis and junction areas extending in between the rows and substantially perpendicular to the longitudinal axis. The first and second absorbent layers may be combined together such that at least a portion of said thermoplastic adhesive material of the first absorbent layer contacts at least a portion of the thermoplastic adhesive material of the second absorbent layer, the absorbent particulate polymer material may be disposed between the first and second substrates in an absorbent particulate polymer material area, the absorbent particulate polymer material may be substantially continuously distributed across the absorbent particulate polymer material area, and the respective patterns may be offset from one another so that the rows of both patterns are substantially parallel to one another and the rows of each pattern fit between the rows of the other of the patterns. Other features and advantages of the invention may be apparent from reading the following detailed description, drawings, and claims.

DETAILED DESCRIPTION OF THE INVENTION

As summarized above, this invention encompasses a method and apparatus for making a disposable absorbent article comprising absorbent particulate polymer material deposited on a substrate and a resulting disposable absorbent article. Embodiments of such method and apparatus and resulting disposable absorbent articles are described hereinbelow after the following definitions.

Definitions

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

Figure 8:
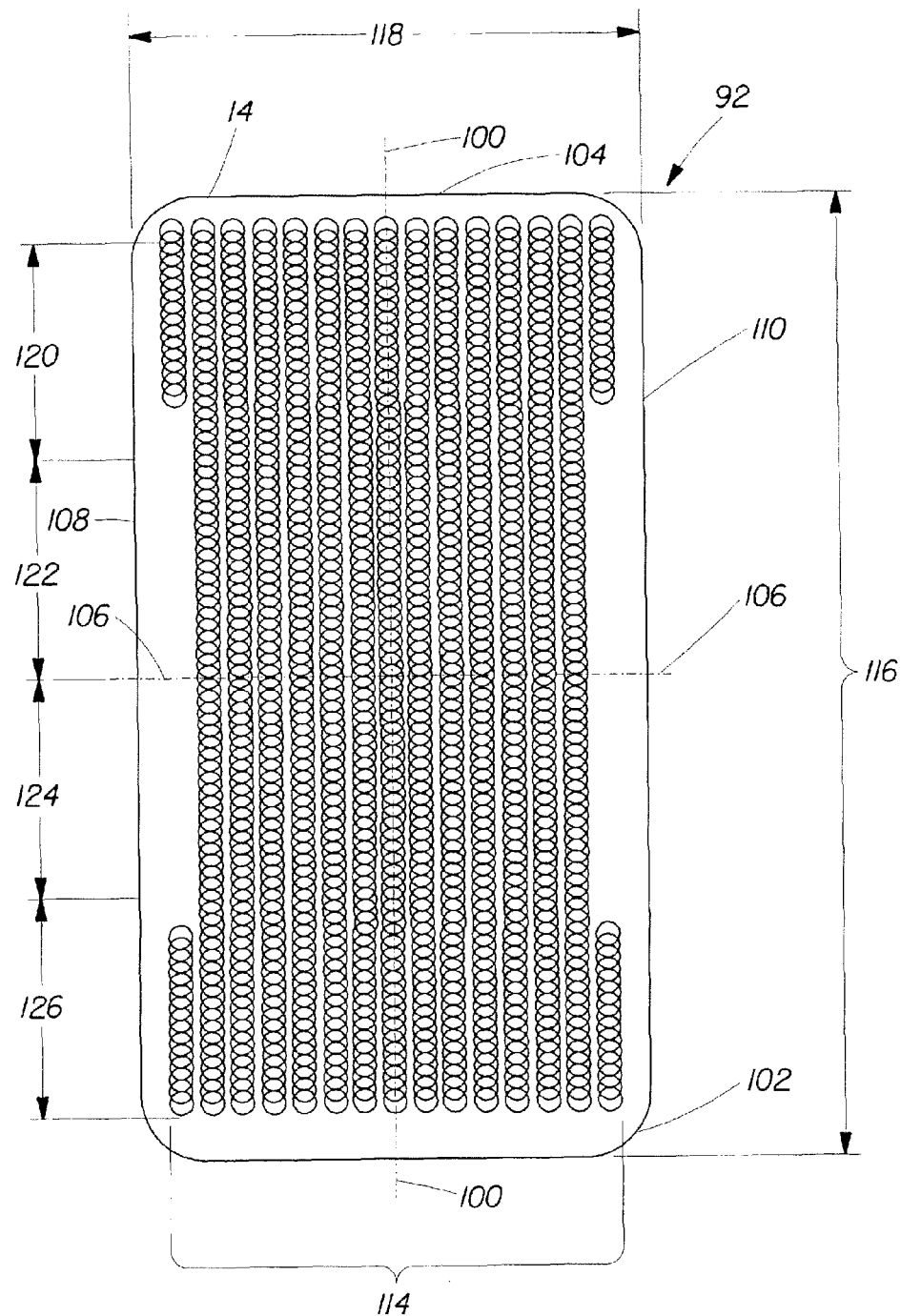
FIG. 8 is a plan view of the absorbent core illustrated in FIG. 7.

"Absorbent particulate polymer material area" as used herein refers to the area of the core wherein the first substrate 64 and second substrate 72 are separated by a multiplicity of superabsorbent particles. In FIG. 8, the boundary of the absorbent particulate polymer material area is defined by the perimeter of the overlapping circles. There may be some extraneous superabsorbent particles outside of this perimeter between the first substrate 64 and second substrate 72.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

Absorbent Articles

Figure 1:
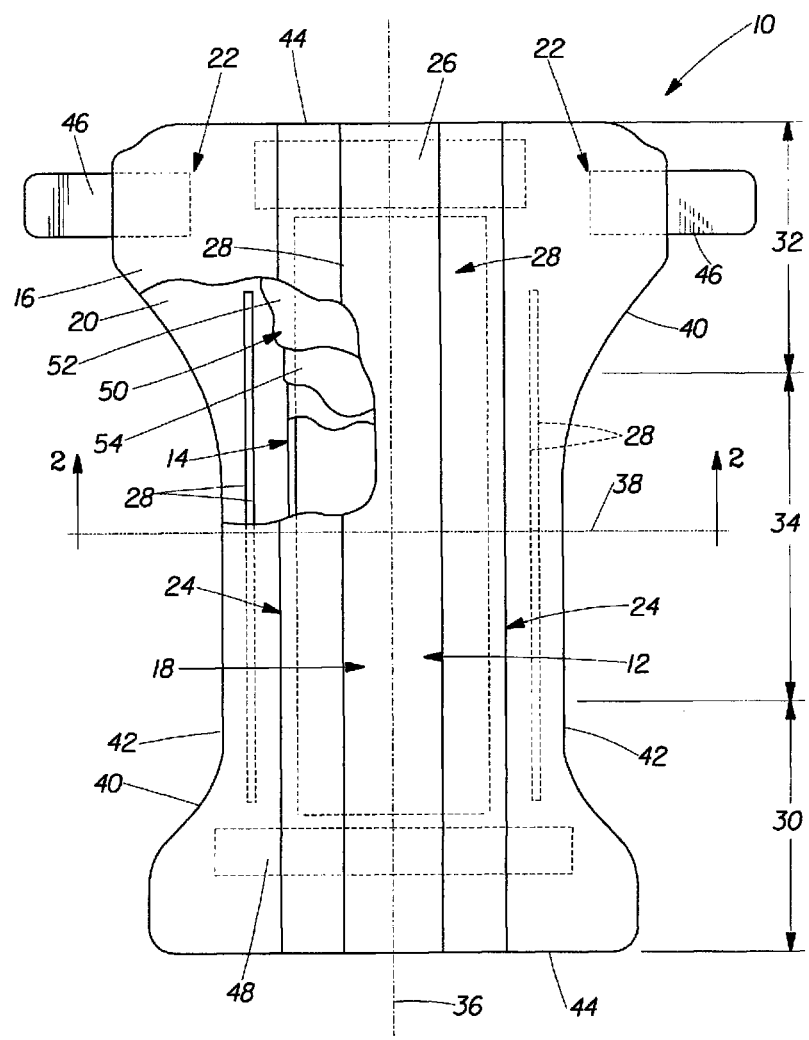
FIG. 1 is a plan view of a diaper in accordance with an embodiment of the present invention.

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 20 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 20 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 $g/24$ $h/m^2$, greater than about 3000 $g/24$ $h/m^2$, greater than about 5000 $g/24$ $h/m^2$, greater than about 6000 $g/24$ $h/m^2$, greater than about 7000 $g/24$ $h/m^2$, greater than about 8000 $g/24$ $h/m^2$, greater than about 9000 $g/24$ $h/m^2$, greater than about 10000 $g/24$ $h/m^2$, greater than about 11000 $g/24$ $h/m^2$, greater than about 12000 $g/24$ $h/m^2$, greater than about 15000 $g/24$ $h/m^2$, measured according to WSP 70.5 (08) at 37.8° C. and 60% Relative Humidity.

Figure 2:
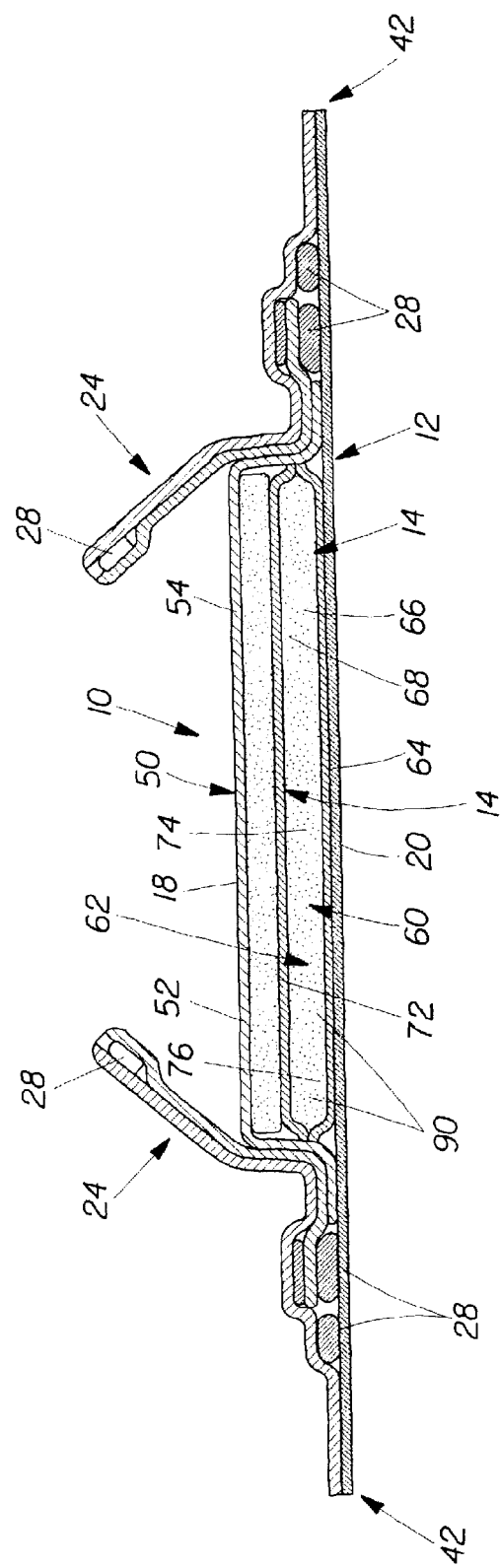
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the topsheet 18, the components of the absorbent core 14, and the backsheet 20. According to a certain embodiment, diaper 10 may also comprise an acquisition system 50 disposed between the liquid permeable topsheet 18 and a wearer facing side of the absorbent core 14. The acquisition system 50 may be in direct contact with the absorbent core. The acquisition system 50 may comprise a single layer or multiple layers, such as an upper acquisition layer 52 facing towards the wearer's skin and a lower acquisition 54 layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In a certain embodiment, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers 52 and 54 may comprise a nonwoven, which may be hydrophilic. Further, according to a certain embodiment, one or both of the upper and lower acquisition layers 52 and 54 may comprise the chemically cross-linked cellulosic fibers, which may or may not form part of a nonwoven material. According to an exemplary embodiment, the upper acquisition layer 52 may comprise a nonwoven, without the cross-linked cellulosic fibers, and the lower acquisition layer 54 may comprise the chemically cross-linked cellulosic fibers. Further, according to an embodiment, the lower acquisition layer 54 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer 54 has a total dry weight, the cross-linked cellulosic fibers are present on a dry weight basis in the upper acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54. According to another embodiment, the cross-linked cellulosic fibers are present on a dry weight basis in the first acquisition layer in an amount from about 80% to about 90% by weight of the lower acquisition layer 54, and the other natural or synthetic polymeric fibers are present on a dry weight basis in the lower acquisition layer 54 in an amount from about 20% to about 10% by weight of the lower acquisition layer 54.

According to a certain embodiment, the lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer 54 has a maximum uptake of about 10 g/g.

A relevant attribute of the upper acquisition layer 54 is its Median Desorption Pressure, MDP. The MDP is a measure of the capillary pressure that is required to dewater the lower acquisition layer 54 to about 50% of its capacity at 0 cm capillary suction height under an applied mechanical pressure of 0.3 psi. Generally, a relatively lower MDP may be useful. The lower MDP may allow the lower acquisition layer 54 to more efficiently drain the upper acquisition material. Without wishing to be bound by theory, a given distribution material may have a definable capillary suction. The ability of the lower acquisition layer 54 to move liquid vertically via capillary forces will be directly impacted by gravity and the opposing capillary forces associated with desorption of the upper acquisition layer. Minimizing these capillary forces may positively impact the performance of the lower acquisition layer 54. However, in a certain embodiment the lower acquisition layer 54 may also have adequate capillary absorption suction in order to drain the layers above (upper acquisition layer 52 and topsheet 18, in particular) and to temporarily hold liquid until the liquid can be partitioned away by the absorbent core components. Therefore, in a certain embodiment, the lower acquisition layer 54 may have a minimum MDP of greater than 5 cm. Further, according to exemplary embodiments, the lower acquisition layer 54 has an MDP value of less than about 20.5 cm $H_2O$, or less than about 19 cm $H_2O$, or less than about 18 cm $H_2O$ to provide for fast acquisition.

The methods for determining MDP and maximum uptake are disclosed in U.S. Patent Application Publication No. 2007/0118087 A1. For example, according to a first embodiment, the lower acquisition layer 54 may comprise about 70% by weight of chemically cross-linked cellulose fibers, about 10% by weight polyester (PET), and about 20% by weight untreated pulp fibers. According to a second embodiment, the lower acquisition layer 54 may comprise about 70% by weight chemically cross-linked cellulose fibers, about 20% by weight lyocell fibers, and about 10% by weight PET fibers. According to a third embodiment, the lower acquisition layer 54 may comprise about 68% by weight chemically cross-linked cellulose fibers, about 16% by weight untreated pulp fibers, and about 16% by weight PET fibers. In one embodiment, the lower acquisition layer 54 may comprise from about 90-100% by weight chemically cross-linked cellulose fibers.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

In certain embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated nonwoven is that disclosed in U.S. Patent Application Publication No. 2004/0158212 entitled "Disposable absorbent article comprising a durable hydrophilic core wrap" to Ekaterina Anatolyevna Ponomarenko and Mattias NMN Schmidt.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and U.S. Patent Application Publication Numbers. 2003/0148684 A1 to Cramer et al. and 2005/0008839 A1 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

According to a certain embodiment, the upper acquisition layer 52 may comprise a material that provides good recovery when external pressure is applied and removed. Further, according to a certain embodiment, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Figure 3:
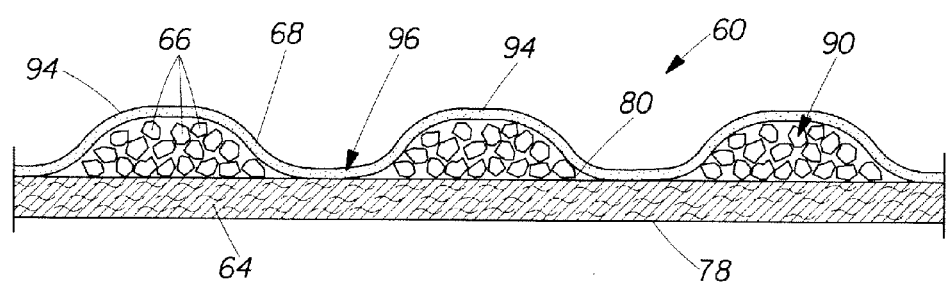
FIG. 3 is a partial longitudinal cross sectional view of an absorbent core layer in accordance with an embodiment of this invention.

The absorbent core 14 in FIGS. 1-8 generally is disposed between the topsheet 18 and the backsheet 20 and comprises two layers, a first absorbent layer 60 and a second absorbent layer 62. As best shown in FIG. 3, the first absorbent layer 60 of the absorbent core 14 comprises a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

Figure 7:
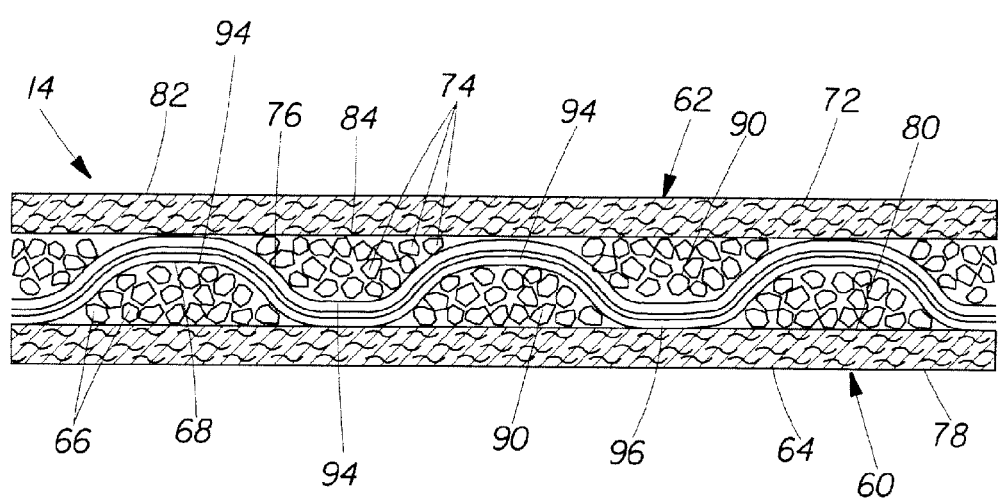
FIG. 7 is a partial longitudinal sectional view of an absorbent core comprising a combination of the first and second absorbent core layers illustrated in FIGS. 5 and 6.

Likewise, as best illustrated in FIG. 7, the second absorbent layer 62 of the absorbent core 14 may also include a substrate 72, an absorbent particulate polymer material 74 on the second substrate 72, and a thermoplastic composition 76 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. Likewise, the substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material, such as those nonwoven materials described above. In certain embodiments, the non-wovens are porous and in one embodiment has a pore size of about 32 microns.

As illustrated in FIGS. 1-8, the absorbent particulate polymer material 66 and 74 is deposited on the respective substrates 64 and 72 of the first and second absorbent layers 60 and 62 in clusters 90 of particles to form a grid pattern 92 comprising rows 94 of the absorbent particulate polymer material 66 and 74 spaced from one another and junction areas 96 between the rows 94. The thermoplastic adhesive material 68 and 76 may not contact the nonwoven substrate or the auxiliary adhesive directly in the rows 94 except perhaps in areas where there is lesser absorbent particulate polymer material 66 and 74; junction areas 96 are areas where the thermoplastic adhesive material does contact the nonwoven substrate or the auxiliary adhesive directly. The junction areas 96 in the grid pattern 92 contain little or no absorbent particulate polymer material 66 and 74. The rows 94 and junction areas 96 are elongate and extend in a cross direction which is substantially perpendicular to the longitudinal axis 100 of the absorbent core 14.

Figure 5:
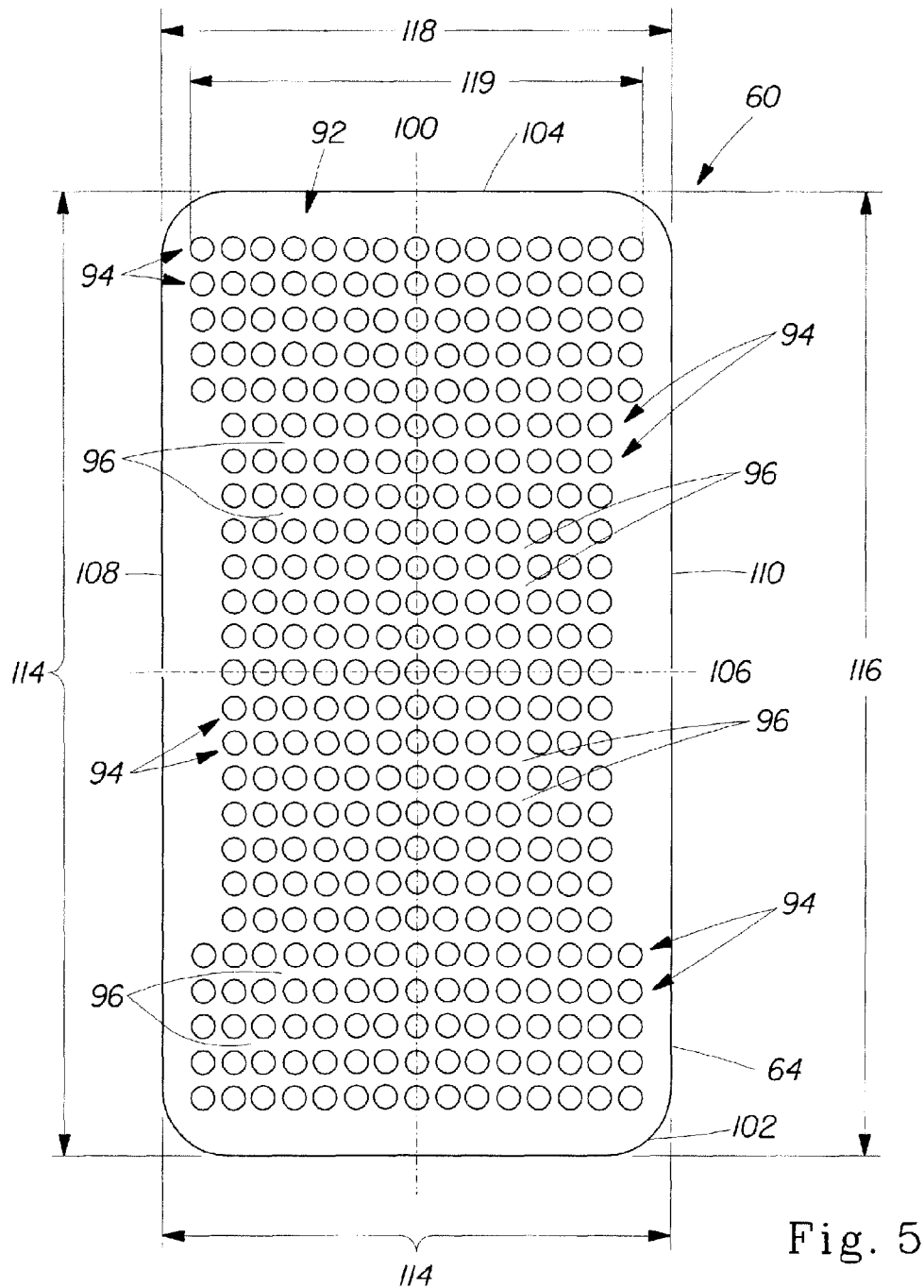
FIG. 5 is a plan view of the absorbent core layer illustrated in FIG. 3.
Figure 6:
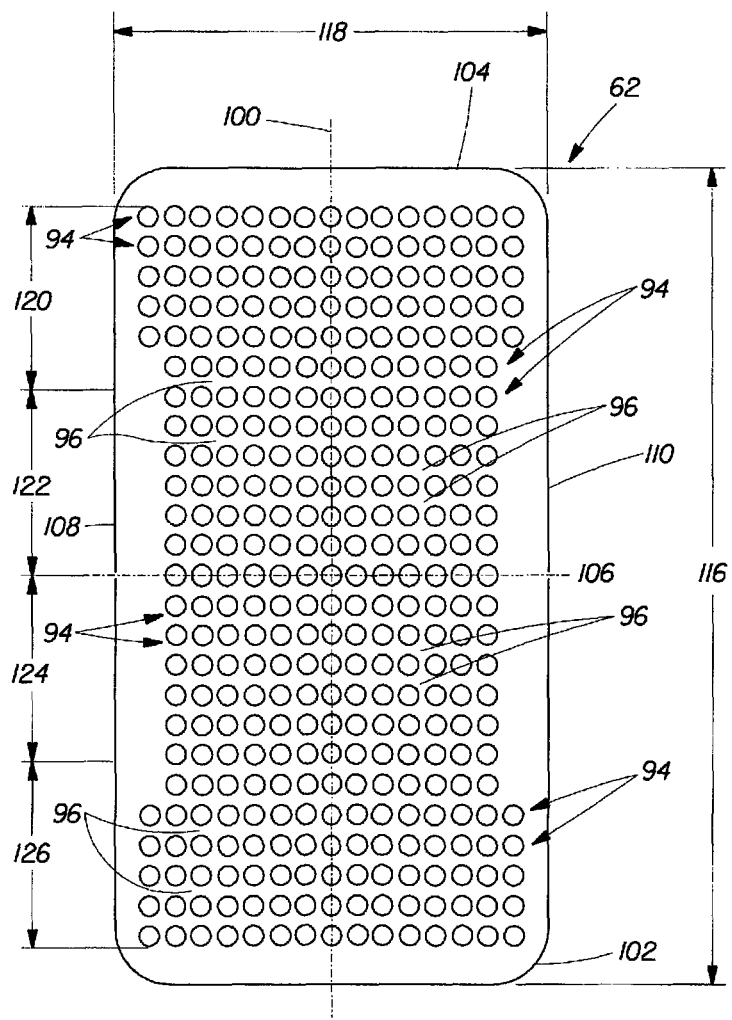
FIG. 6 is a plan view of a second absorbent core layer in accordance with an embodiment of this invention.

The grid pattern shown in FIGS. 5, 6, and 8 is a rectangular grid with regular spacing and size of the rows. Other grid patterns including hexagonal, rhombic, orthorhombic, parallelogram, triangular, square, and combinations thereof may also be used. According to a certain embodiment, the spacing between the rows 94 may be regular.

The size of the rows 94 in the grid patterns 92 may vary. According to certain embodiments, the width 119 of the rows 94 in the grid patterns 92 ranges from about 8 mm to about 12 mm. In a certain embodiment, the width of the rows 94 is about 10 mm. The junction areas 96, on the other hand, in certain embodiments, have a width or larger span of less than about 3 mm to about 3 mm. According to a certain embodiment, the absorbent particulate polymer 66 and 74 form substantially continuous rows, but the clusters 90 of absorbent particulate polymer 66 and 74 may form rows of intermittent absorbent particulate polymer 66 and 74 according to other embodiments.

As shown in FIGS. 5, 6 and 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 is arranged on the substrates 64 and 72 of the respective absorbent layers 60 and 62 such that the rows 94 and junction areas 96 are substantially perpendicular to the longitudinal axis 100 of the absorbent core 14. Accordingly, certain embodiments of the absorbent core 14 may be made so that boundaries of the grid patterns 92 of the absorbent layers 60 and 62 are substantially straight.

As best seen in FIGS. 7 and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In a certain embodiment, however, the absorbent particulate polymer material area 114 extends substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length of the absorbent core 14. The length of the absorbent core 14 extends along the longitudinal axis 100 of the absorbent core 14 and is parallel thereto. The respective grid patterns 92 may be offset in the direction of the longitudinal axis 100 (the machine direction) such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 due to the alternating rows 94 and junction areas 96. In a certain embodiment, the grid patterns may be offset such that the rows 94 of the first absorbent layer 60 face the junction areas 96 of the second absorbent layer 62 and the rows 94 of the second absorbent layer 62 face the junction areas 96 of the first absorbent layer 60. In other words, the rows 94 and junction areas 96 of the first absorbent layer 60 are substantially parallel to the rows 94 and junction areas 96 of the second absorbent layer 62 and the rows 94 of the first absorbent layer 60 are disposed at least partially between the rows 94 of the second absorbent layer 62. When the rows 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14. In a certain embodiment, respective grid patterns 92 of the first and second absorbent layer 60 and 62 may be substantially the same and the respective patterns are offset one half cycle relative to one another in the machine direction.

In the latter case, the respective patterns 92 of absorbent particulate polymer 66 and 74 may also be offset in a direction substantially perpendicular to the longitudinal axis 100 (the cross direction) so that the resulting combination of absorbent particulate polymer material 66 and 74 is a substantially continuous layer of absorbent particular polymer material across the absorbent particulate polymer material area 114 of the absorbent core 14.

In a certain embodiment as illustrated in FIG. 8, the amount of absorbent particulate polymer material 66 and 74 may vary along the length 116 of the grid pattern 92. In a certain embodiment, the grid pattern may be divided into absorbent zones 120, 122, 124, and 126, in which the amount of absorbent particulate polymer material 66 and 74 varies from zone to zone. As used herein, "absorbent zone" refers to a region of the absorbent particulate polymer material area having boundaries that are perpendicular to the longitudinal axis shown in FIG. 8. The amount of absorbent particulate polymer material 66 and 74 may, in a certain embodiment, gradually transition from one of the plurality of absorbent zones 120, 122, 124, and 126 to another. This gradual transition in amount of absorbent particulate polymer material 66 and 74 may reduce the possibility of cracks forming in the absorbent core 14.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 consists essentially of the first and second substrates 64 and 72, the absorbent particulate polymer material 66 and 74, and the thermoplastic adhesive composition 68 and 76. In an embodiment, the absorbent core 14 may be substantially cellulose free.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

The absorbent particulate polymer material area, according to an exemplary embodiment, may have a relatively narrow width in the crotch area of the absorbent article for increased wearing comfort. Hence, the absorbent particulate polymer material area, according to an embodiment, may have a width as measured along a transverse line which is positioned at equal distance to the front edge and the rear edge of the absorbent article, which is less than about 100 mm, 90 mm, 80 mm, 70 mm, 60 mm or even less than about 50 mm.

It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

Figure 4:
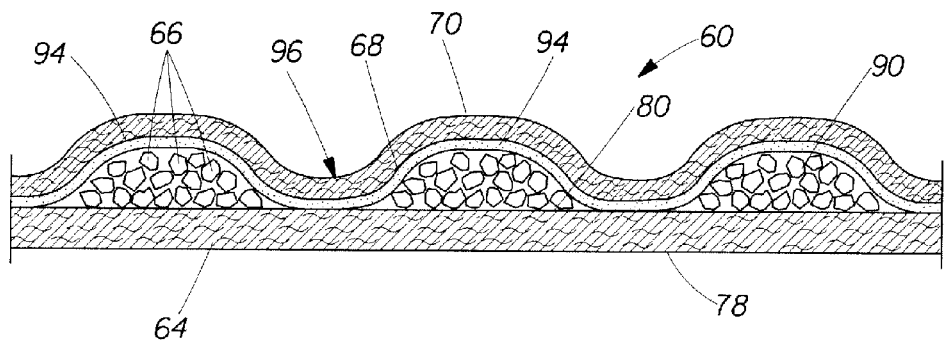
FIG. 4 is a partial longitudinal cross sectional view of an absorbent core layer in accordance with another embodiment of this invention.

The thermoplastic adhesive material 68 and 76 may serve to cover and at least partially immobilize the absorbent particulate polymer material 66 and 74. In one embodiment of the present invention, the thermoplastic adhesive material 68 and 76 can be disposed essentially uniformly within the absorbent particulate polymer material 66 and 74, between the polymers. However, in a certain embodiment, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4, and 7 show such a structure, and in that structure, the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet, such that the absorbent core 14 achieves an absorbent particulate polymer material loss of no more than about 70%, 60%, 50%, 40%, 30%, 20%, 10% according to the Wet Immobilization Test described herein. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

Without wishing to be bound by theory, it has been found that those thermoplastic adhesive materials which are most useful for immobilizing the absorbent particulate polymer material 66 and 74 combine good cohesion and good adhesion behavior. Good adhesion may promote good contact between the thermoplastic adhesive material 68 and 76 and the absorbent particulate polymer material 66 and 74 and the substrates 64 and 72. Good cohesion reduces the likelihood that the adhesive breaks, in particular in response to external forces, and namely in response to strain. When the absorbent core 14 absorbs liquid, the absorbent particulate polymer material 66 and 74 swells and subjects the thermoplastic adhesive material 68 and 76 to external forces. In certain embodiments, the thermoplastic adhesive material 68 and 76 may allow for such swelling, without breaking and without imparting too many compressive forces, which would restrain the absorbent particulate polymer material 66 and 74 from swelling.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6° C.<Tg<16° C.$ In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 68 and 76 is present in the form of fibers. In some embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other non-woven layer, such layers may be pre-treated with an auxiliary adhesive.

In certain embodiments, the thermoplastic adhesive material 68 and 76 will meet at least one, or several, or all of the following parameters:

An exemplary thermoplastic adhesive material 68 and 76 may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

Figure 9:
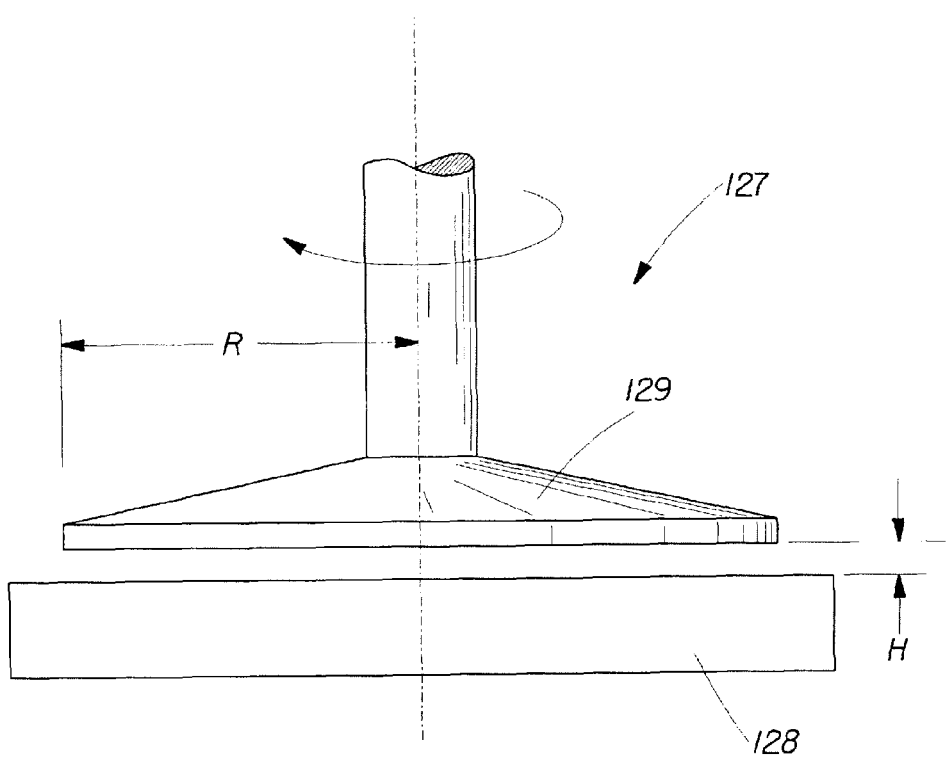
FIG. 9 is a schematic representation of a rheometer.

G' is measured using a rheometer as schematically shown in FIG. 9 for the purpose of general illustration only. The rheometer 127 is capable of applying a shear stress to the adhesive and measuring the resulting strain (shear deformation) response at constant temperature. The adhesive is placed between a Peltier-element acting as lower, fixed plate 128 and an upper plate 129 with a radius R of e.g., 10 mm, which is connected to the drive shaft of a motor to generate the shear stress. The gap between both plates has a height H of e.g., 1500 micron. The Peltier-element enables temperature control of the material (+0.5° C.). The strain rate and frequency should be chosen such that all measurements are made in the linear viscoelastic region.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates 64 and 72 by any suitable means, but according to certain embodiments, may be applied in about 0.5 to about 1 mm wide slots spaced about 0.5 to about 2 mm apart.

The cover layer 70 shown in FIG. 4 may comprise the same material as the substrates 64 and 72, or may comprise a different material. In certain embodiments, suitable materials for the cover layer 70 are the non-woven materials, typically the materials described above as useful for the substrates 64 and 72.

Method and Apparatus for Making Absorbent Articles

Figure 10:
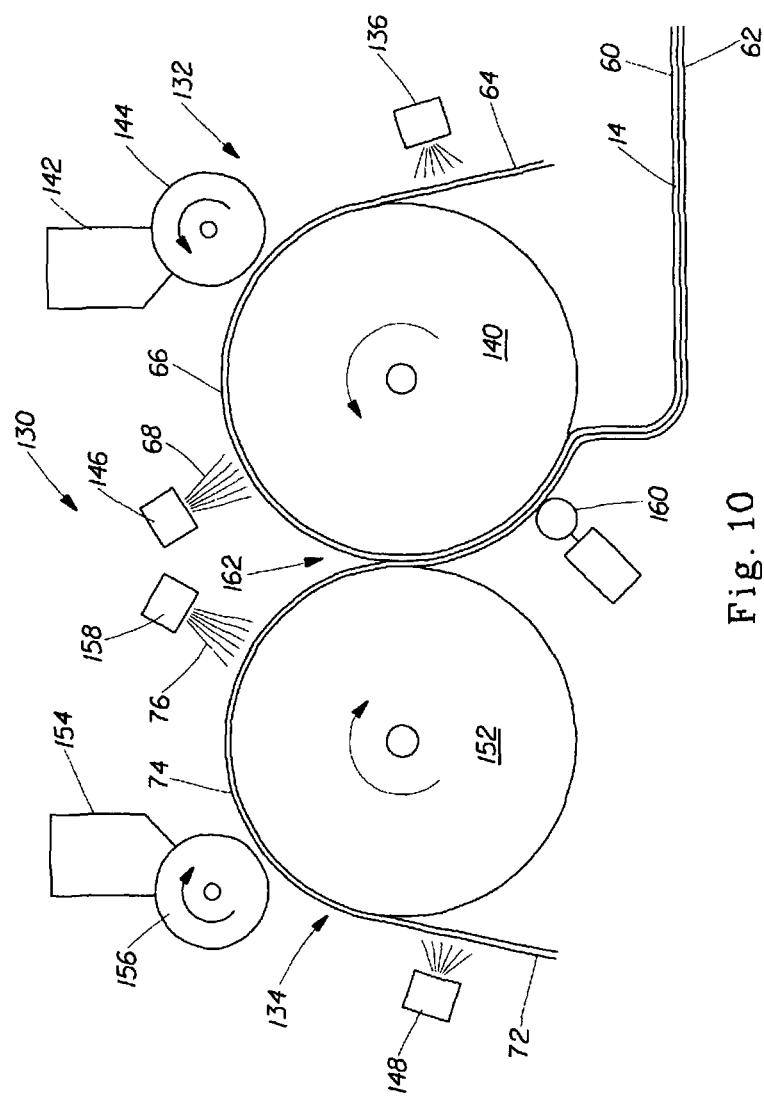
FIG. 10 is a schematic illustration of a process for making an absorbent core in accordance with an embodiment of this invention.

A printing system 130 for making an absorbent core 14 in accordance with an embodiment of this invention is illustrated in FIG. 10 and may generally comprise a first printing unit 132 for forming the first absorbent layer 60 of the absorbent core 14 and a second printing unit 134 for forming the second absorbent layer 62 of the absorbent core 14.

The first printing unit 132 may comprise a first auxiliary adhesive applicator 136 for applying an auxiliary adhesive to the substrate 64, which may be a nonwoven web, a first rotatable support roll 140 for receiving the substrate 64, a first absorbent particulate polymer feeder (hopper) 142 for holding absorbent particulate polymer material 66, a first printing roll 144 for transferring the absorbent particulate polymer material 66 to the substrate 64, and a first thermoplastic adhesive material applicator 146 for applying the thermoplastic adhesive material 68 to the substrate 64 and the absorbent particulate polymer 66 material thereon.

The second printing unit 134 may comprise a second auxiliary adhesive applicator 148 for applying an auxiliary adhesive to the second substrate 72, a second rotatable support roll 152 for receiving the second substrate 72, a second absorbent particulate polymer feeder (hopper) 154 for holding the absorbent particulate polymer material 74, a second printing roll 156 for transferring the absorbent particulate polymer material 74 from the hopper 154 to the second substrate 72, and a second thermoplastic adhesive material applicator 158 for applying the thermoplastic adhesive material 76 to the second substrate 72 and the absorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second thermoplastic adhesive material applicators 146 and 158 may be a nozzle system which can provide a relatively thin but wide curtain of thermoplastic adhesive material.

Figure 11:
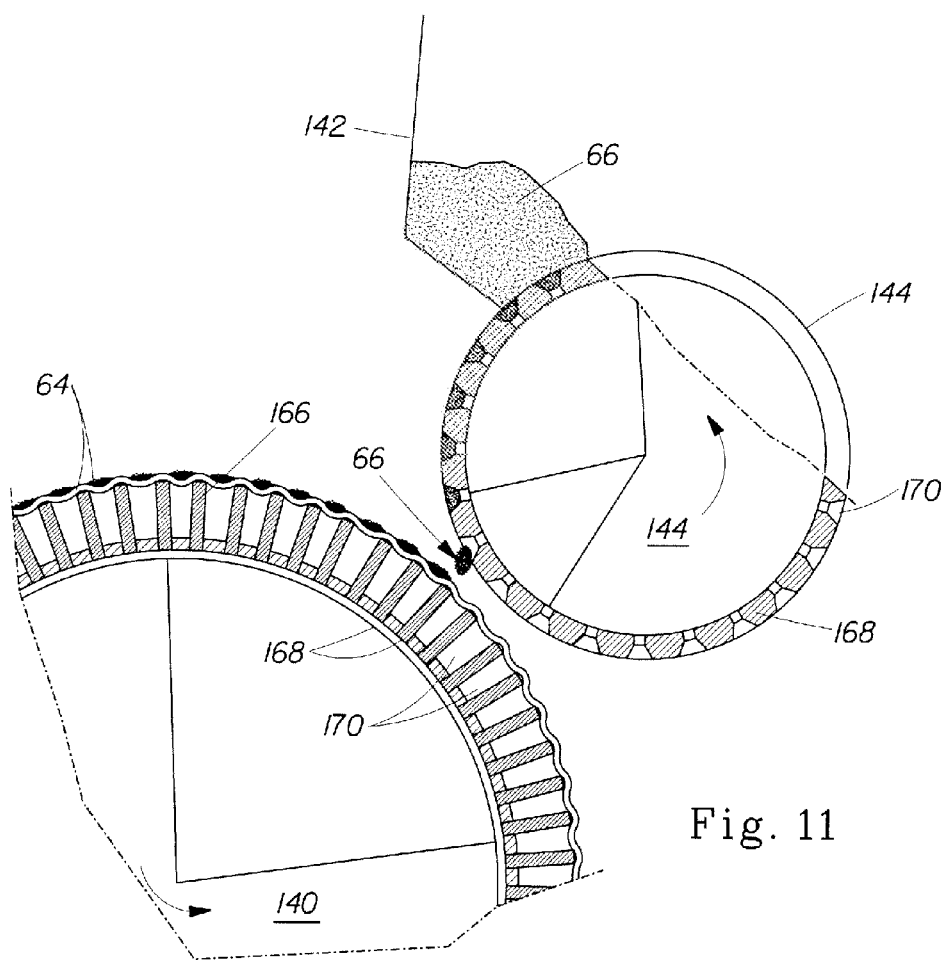
FIG. 11 is a partial sectional view of an apparatus for making an absorbent core in accordance with an embodiment of this invention.
Figure 12:
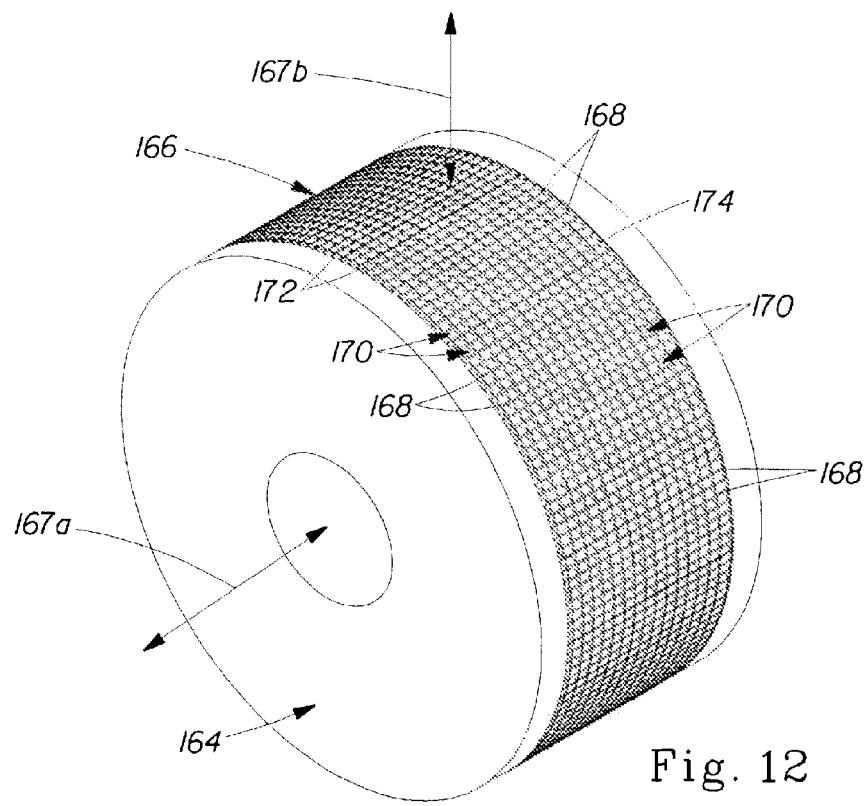
FIG. 12 is a perspective view of a supporting roll illustrated in FIG. 11.
Figure 13:
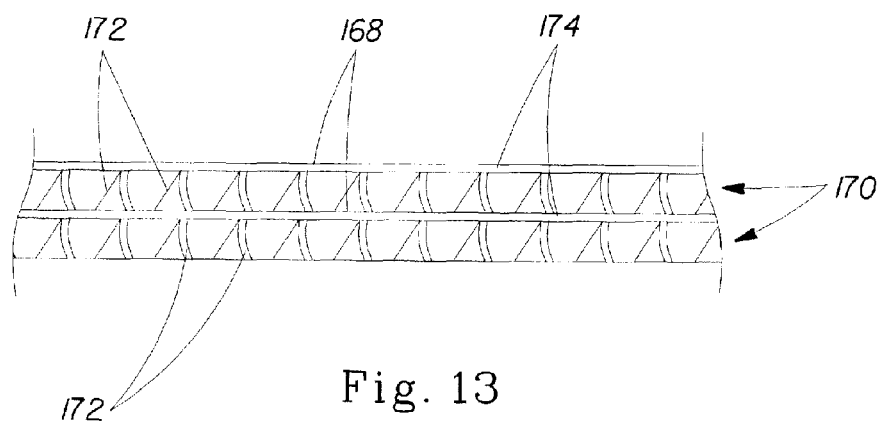
FIG. 13 is a partial perspective view of a grid which forms part of the supporting roll illustrated in FIG. 12.

Turning to FIG. 11, portions of the first hopper 142, first support roll 140, and first printing roll 144 are illustrated. As also shown in FIG. 12, the first rotatable support roll 140, which has the same structure as the second rotatable support roll 152, comprises a rotatable drum 164 and a peripheral vented support grid 166 for receiving the first substrate 64. The first vented support grid 166 extends in a cross direction 167a parallel to an axis of rotation of the first support roll 140 and a machine direction 167b substantially perpendicular to the cross direction 167a. The vented support grid 166 may include a first plurality of cross bars 168 extending substantially parallel to and spaced from one another so as to form channels 170 extending between the first plurality of cross bars 168. The first plurality of cross bars 168 extend in the cross direction 167a of the first vented support grid 166 and are spaced from one another so that the channels 170 extend between the first plurality of cross bars 168 in the cross direction 167a of the first vented support grid 166. As shown in FIG. 13, the first vented support grid 166 further comprises a plurality of spacers 172 spaced from one another and extending between the first plurality of cross bars 168 in the machine direction 167b of the first vented support grid 166. The first plurality of cross bars 168 each have a substantially straight outwardly facing edge 174 extending across substantially the entire first vented support grid 166.

Figure 14:
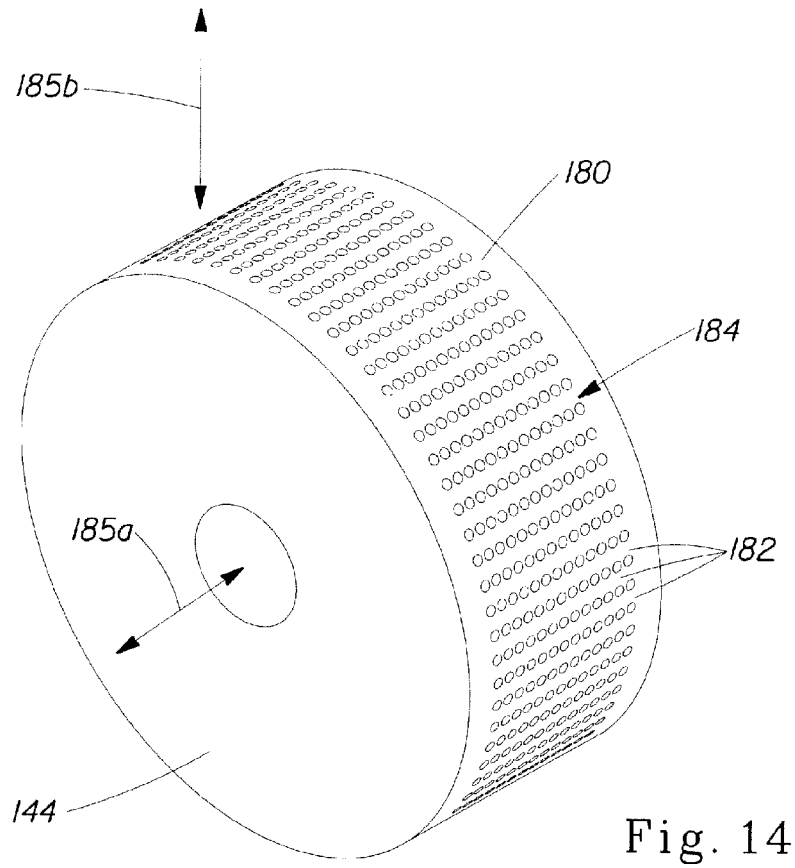
FIG. 14 is a perspective view of a printing roll illustrated in FIG. 11.
Figure 15:
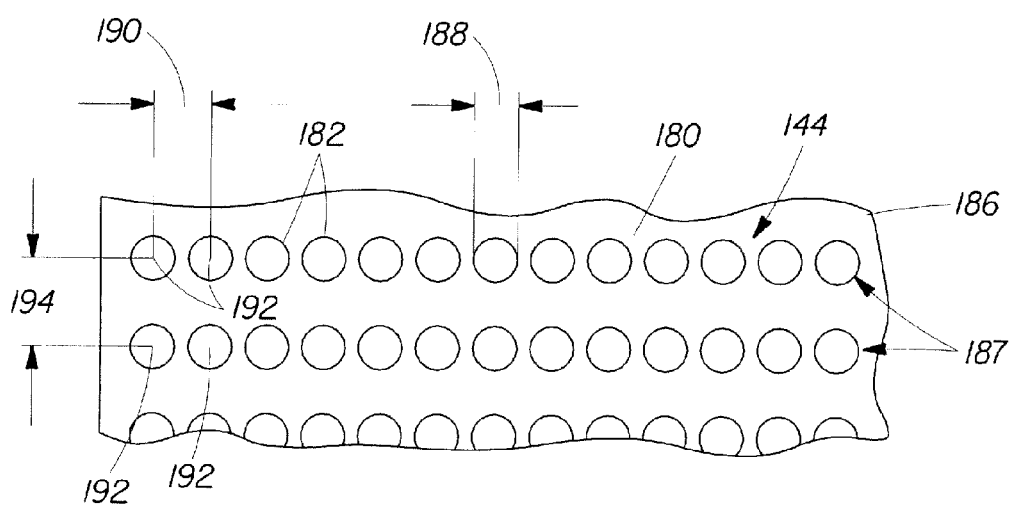
FIG. 15 is a partial perspective view of the printing roll illustrated in FIG. 14 showing absorbent particulate polymer material reservoirs.
Figure 16:
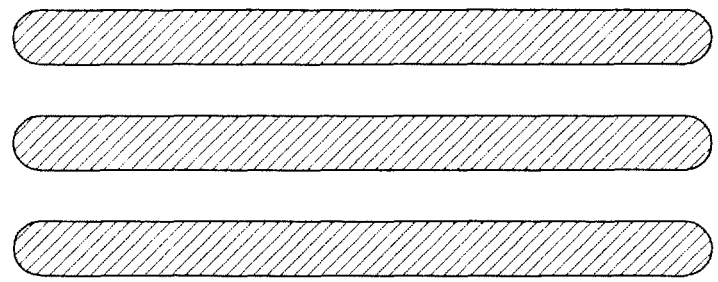
FIG. 16 is a partial perspective view of an alternative printing roll showing absorbent particulate polymer material reservoirs.
Figure 17:
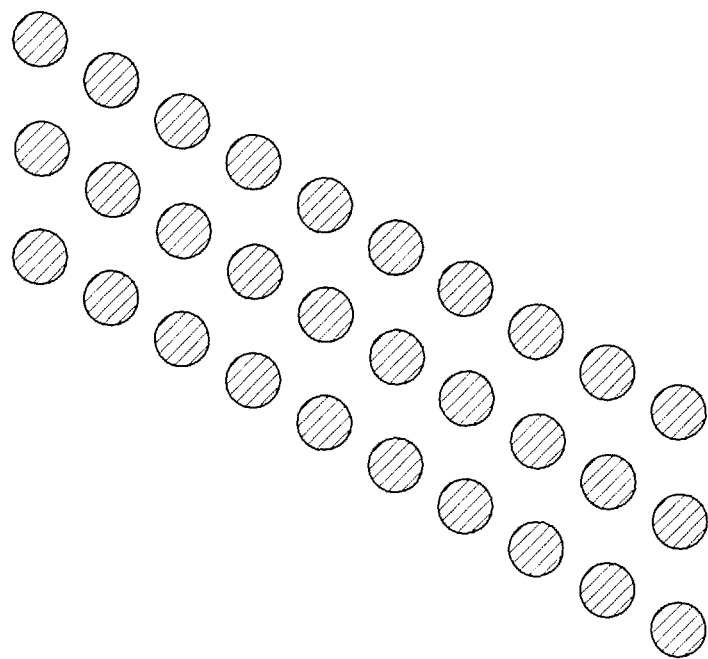
FIG. 17 is a partial perspective view of an alternative printing roll showing absorbent particulate polymer material reservoirs.

As also illustrated in FIG. 14, the first printing roll 144, which has the same structure as the second printing roll 156, comprises a rotatable drum 180 and a plurality of absorbent particulate polymer material reservoirs 182 in a first peripheral surface 184 of the drum 180. The reservoirs 182, best illustrated in FIG. 15, may have a variety of shapes, including cylindrical, conical, or any other shape. FIG. 16 and FIG. 17 demonstrate additional embodiments contemplated by the invention. FIG. 16 shows a partial perspective view of an alternative printing roll showing absorbent particulate polymer material reservoirs. In this embodiment, the individual round holes in the print roll are replaced with single or multiple slots. FIG. 17 demonstrates that the orientation of the bars in the laydown drum and/or the print roll can be different from perpendicular to the MD, resulting in a pattern as shown in FIG. 17. Further, a combination of these embodiments is also contemplated by the invention.

The first peripheral surface 184 extends in a cross direction 185a parallel to an axis of rotation of the first printing roll 144 and a machine direction 185b substantially perpendicular to the cross direction 185a. The first plurality of reservoirs 182 in the first peripheral surface 184 are arranged in an array 186 comprising rows 187 extending substantially parallel to and spaced from one another. The first support roll 140 and first printing roll 144 are arranged such that the first plurality of cross bars 168 are substantially parallel to the rows 187 of the first plurality of reservoirs 182 in the first peripheral surface 184, so that, when the first printing roll 144 rotates, the first plurality of reservoirs 182 receive absorbent particulate polymer material 66 from the first absorbent particulate polymer material feeder 142 and deposit the absorbent particulate polymer material 66 on the first substrate 64 in a first pattern 92 such that the absorbent particulate polymer material 66 collects in rows 94 on the first substrate 64 formed between the first plurality of cross bars 168. The rows 187 of first plurality of reservoirs 182 extend in the cross direction 185a of the first peripheral surface 184 and are spaced from one another in the machine direction 185b of the first peripheral surface 184. The first support roll 140 and the first printing roll 144 are arranged such that the machine direction 167b of the first vented support grid 166 is substantially parallel to the machine direction 185b of the first peripheral surface 184 and the cross direction 167a of the first vented support grid 166 is substantially parallel to the cross direction 185a of the first peripheral surface 184.

According to a certain embodiment, the plurality of reservoirs 182 in the first printing roll 144 each have a diameter 188 of about 3 to about 8 mm or about 4 to about 6 mm, a spacing 190 in a cross direction 185a of about 5.5 to about 10 mm or about 6 to about 8 mm or about 7.6 mm from reservoir center 192 to reservoir center 192, and a spacing 194 in a machine direction 185b of about 8 to about 10 mm from reservoir center 192 to reservoir center 192. According to a certain embodiment, the reservoirs 182 may have a depth of about 2 mm. The size of the reservoirs 182 may vary across the array 186 as desired to affect the basis weight distribution of the absorbent particulate polymer material 66 across the absorbent particulate polymer material area 114 of the absorbent core 14.

In operation, the printing system 130 receives the first and second substrate 64 and 72 into the first and second printing units 132 and 134, respectively, the first substrate 64 is drawn by the rotating first support roll 140 past the first auxiliary adhesive applicator 136 which applies the first auxiliary adhesive to the first substrate 64 in a pattern such as described hereinabove. The first substrate 64 is disposed on the first vented support grid 166 so that the first substrate 64 directly contacts at least some of the first plurality of cross bars 168 and, in a certain embodiment, the first substrate 64 directly contacts the outwardly facing edges 174 of the first plurality of cross bars 168 across substantially the entire length of the vented support grid 166. According to a certain embodiment, about 8% of the area of the first substrate 64 contacts the outwardly facing edges 174 of the first plurality of cross bars 168.

A vacuum (not shown) within the first support roll 140 draws the first substrate 64 against the vertical support grid 166 and holds the first substrate 64 against the first support roll 140. This presents an uneven surface on the first substrate 64. Due to gravity, or by using the vacuum means, the substrate 64 will follow the contours of the uneven surface and thereby the substrate 64 will assume a mountain and valley shape with the mountains corresponding to the first plurality of cross bars 168 and the valleys corresponding to the channels 170 therebetween. The absorbent particulate polymer material 66 may accumulate in the channels 170 presented by the substrate 64 and form the rows 94 in the absorbent particulate polymer material pattern 92. The first support roll 140 then carries the first substrate 64 past the rotating first printing roll 144 which transfers the absorbent particulate polymer material 66 from the first hopper 142 to the first substrate 64 in the grid pattern 92 which is best illustrated in FIGS. 5 and 6. The support roll 140 then carries the printed first substrate 64 past the thermoplastic adhesive material applicator 136 which applies the thermoplastic adhesive material 68 to cover the absorbent particulate polymer material 66 on the first substrate 64.

Hence, the uneven surface of the vented support grid 166 of the support rolls 140 and 152 determines the distribution of absorbent particulate polymeric material 66 and 74 throughout the absorbent core 14 and likewise determines the pattern of junction areas 96.

Meanwhile, the second rotatable support roll draws the second substrate 72 past the second auxiliary adhesive applicator 148 which applies an auxiliary adhesive to the second substrate 72 in a pattern such as is described hereinabove. The second rotatable support roll 152 then carries the second substrate 72 past the second printing roll 156 which transfers the absorbent particulate polymer material 74 from the second hopper 154 to the second substrate 72 and deposits the absorbent particulate polymer material 74 in the grid pattern 92 on the second substrate 72 in the same manner as described with regard to the first printing unit 132 above. The second thermoplastic adhesive material applicator 158 then applies the thermoplastic adhesive material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form the absorbent core 14.

In an optional further process step a cover layer 70 may be placed upon the substrates 64 and 72, the absorbent particulate polymer material 66 and 74, and the thermoplastic adhesive material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

Embodiments described hereinabove may provide good uniformity of absorbent particulate polymer material distribution across the absorbent particulate polymer material area 114 of the absorbent core 14 at lesser blow off air pressure and lesser vacuum applied by the support rolls 140 and 152 and may reduce amount of absorbent particulate polymer material that needs to be recycled while maintaining or even enhancing wet immobilization of the absorbent particulate polymer material. In addition, process control may be simplified because little or no offset between the first and second absorbent layers 60 and 62 is required in the cross direction. Furthermore, because the rows 94 of absorbent particulate polymer material extend in a cross direction which is substantially perpendicularly to the longitudinal axis 100 of the absorbent core 14, the boundaries of the absorbent particulate polymer material pattern The test method and apparatuses described below may be useful in testing embodiments of this invention:

Wet Immobilization Test

Equipment
- Graduated Cylinder
- Stop watch (±0.1 sec)
- Scissors
- Light Box
- Pen
- Test solution: 0.90% saline solution at 37° C.
- Metal ruler traceable to NIST, DIN, JIS or other comparable National Standard
- PVC/metal dishes with a flat surface inside and a minimum length of the core bag length (n) to be measured and a maximum length n+30 mm, width of 105±5 mm, height of 30-80 mm or equivalent
- Electronic Force Gauge (Range 0 to 50 Kg)
- Wet Immobilization Impact Tester Equipment (WAIIT), Design package number: BM-00112.59500-R01 available from T.M.G. Technisches Buero Manfred Gruna Facilities:
Standard laboratory conditions, temperature: 23° C.±2° C., relative humidity: <55%

Sample Preparation
1. Open the product, topsheet side up.
2. Unfold the diaper and cut the cuff elastics approximately every 2.5 cm to avoid chassis tension.
3. For pull-up products open the side seams and remove the waistbands.
4. Lay the core bag flat and rectangular topsheet side up onto the light box surface without any folds.
5. Switch on the light box to clearly identify the absorbent core outer edges.
6. With a ruler, draw a line at the front and back absorbent core outer edges.
7. Measure the distance (A), between the two markers and divide the value by 2, this will be calculated distance (B).
8. Measure the calculated distance (B) from front marker towards the middle of the core bag and mark it. At this marker draw a line in the cross direction.

Test Procedure

WAIIT Calibration:
1. Make sure that the sliding board is in the lower position. Open the front door of the WAIIT tester and connect the force gauge hook to the upper sample clamp of the WAIIT. Make sure that the clamp is closed before connecting the spring-balance.
2. Use both hands on the spring-balance to lift continuously and as slowly as possible up the sliding board towards the upper position. Record the average value ($m_1$) during the execution to the nearest 0.02 kg.
3. Guide down the sliding board as slowly as possible to the lower position and record the average value ($m_2$) read off during execution to the nearest 0.02 kg.
4. Calculate and report the delta of $m_1-m_2$ to the nearest 0.01 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings:
Drop height is 50 cm.
Diaper load ($l_D$) is 73% of the core capacity (cc); $l_D=0.73\times cc$.

Core capacity (cc) is calculated as: $cc=m_{SAP}\times SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258. The mass of the superabsorbent polymer present in the diaper is the average mass present in ten products.

Test Execution:
1. Reset the balance to zero (tare), put the dry core bag on the balance, weigh and report it to the nearest 0.1 g.
2. Measure the appropriate volume Saline (0.9% NaCl in deionized water) with the graduated cylinder.
3. Lay the core bag, topsheet side up, flat into the PVC dish. Pour the saline evenly over the core bag.
4. Take the PVC dish and hold it slanting in different directions, to allow any free liquid to be absorbed. Products with poly-backsheet need to be turned after a minimum waiting time of 2 minutes so that liquid under the backsheet can be absorbed. Wait for 10 minutes (+/−1 minute) to allow all saline to be absorbed. Some drops may retain in the PVC dish. Use only the defined PVC/metal dish to guarantee homogenous liquid distribution and less retained liquid.
5. Reset the balance to zero (tare), put the wet core bag on the balance. Weigh and report it to the nearest 0.1 g. Fold the core bag just once to make it fit on the balance. Check to see if the wet core bag weight is out of limit (defined as "dry core bag weight+diaper load±4 ml"). For example, 12 g dry core bag weight+150 ml load=162 g wet core bag weight. If the actual wet weight on the scale is between 158 g and 166 g, the pad can be used for shaking Otherwise scrap the pad and use the next one.
6. Take the loaded core bag and cut the pad along the marked line in the cross direction.
7. Put the back of the wet core bag onto the balance ($m_1$). Weigh and report it to the nearest 0.1 g.
8. Take the wet core and clamp the end seal side in the top clamp of the sample holder of the WAIIT (open end of the core oriented down). Next, clamp both sides of the core with the side clamps of the sample holder making sure that the product is fixed to the sample holder along the whole product length. Make sure not to clamp the absorbent core, only the nonwoven; for some products this means securing the product with only the barrier leg cuff.
9. Lift up the sliding board to the upper position by using both hands until the board is engaged.
10. Close the safety front door and release the slide blade.
11. Reset the balance to zero (tare), take the tested core bag out of the WAIIT and put it on the balance ($m_2$). Report the weight to the nearest 0.1 g.
12. Repeat steps 7 to 11 with front of the wet core bag.

Reporting:
1. Record the dry core bag weight to the nearest 0.1 g.
2. Record the wet weight before ($m_{1\,front/back}$) and after ($m_{2\,front/back}$) testing, both to the nearest 0.1 g.
3. Calculate and report the average weight loss ($\Delta m$) to the nearest 0.1 g: $\Delta m=(m_{1front}+m_{1back})-(m_{2front}+m_{2back})$
4. Calculate and report the weight loss in percent to the nearest 1%, ($\Delta m_{rel}$): $(\Delta m_{rel})=(((m_{1front}+m_{1back})-(m_{2front}+m_{2back}))\times 100)/(m_{1front}+m_{1back})$ 5. Calculate and report Wet Immobilization (WI) as:
   WI=100%−Δm$_{rel}$ All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a disposable absorbent article comprising:
   providing a first support comprising a first grid including a first plurality of cross bars extending substantially parallel to and spaced from one another so as to form channels extending between the first plurality of cross bars, wherein the first plurality of cross bars each have a substantially straight outwardly facing edge extending across substantially the entire first grid;
   providing a first printing roll having a first peripheral surface and a first plurality of reservoirs in the first peripheral surface arranged in an array comprising rows extending substantially parallel to and spaced from one another; wherein the first plurality of reservoirs have a diameter of about 3 to about 8 mm, a spacing in a cross-direction of about 5.5 to about 10 mm from reservoir center to reservoir center and a spacing in a machine direction of about 8 to about 10 mm from reservoir center to reservoir center;
   depositing absorbent particulate polymer material from the first plurality of reservoirs onto a first substrate disposed on the first grid, while the first support and first printing roll are arranged such that the first plurality of cross bars are substantially parallel to the rows of the first plurality of reservoirs, the absorbent particulate polymer material being deposited on the first substrate in a first pattern such that the absorbent particulate polymer material collects in rows on the first substrate formed between the first plurality of cross bars; and
   depositing a thermoplastic adhesive material on the absorbent particulate polymer material and the first substrate to cover the absorbent particulate polymer material on the first substrate and form a first absorbent layer;
   providing a second support comprising a second grid including a second plurality of cross bars extending substantially parallel to and spaced from one another so as to form channels extending between the second plurality of cross bars;
   providing a second printing roll having a second peripheral surface and a second plurality of reservoirs in the second peripheral surface arranged in an array comprising rows extending substantially parallel to and spaced from one another;
   depositing absorbent particulate polymer material from the second plurality of reservoirs onto a second substrate disposed on the second grid, while the second support and second printing roll are arranged such that the second plurality of cross bars are substantially parallel to the rows of the second plurality of reservoirs, the absorbent particulate polymer material being deposited on the second substrate in a second pattern such that the absorbent particulate polymer material collects in rows on the second substrate formed between the second plurality of cross bars of the second support;
   depositing a thermoplastic adhesive material on the absorbent particulate polymer material and the second substrate to cover the absorbent particulate polymer material on the second substrate and form a second absorbent layer;
   combining said first and second absorbent layers together in juxtaposed relation in a nip between said first and second supports.

2. The method of claim 1 wherein:
   the first grid of the first support extends in a machine direction and the cross direction substantially perpendicular to the machine direction and the first plurality of cross bars extend in the cross direction of the first grid and spaced from one another so that the channels extend between the first plurality of cross bars in the cross direction of the first grid;
   the peripheral surface of the first printing roll extends in a machine direction and a cross direction substantially perpendicular to the machine direction, the rows of first plurality of reservoirs extend in the cross direction of the first peripheral surface and are spaced from one another in the machine direction of the first peripheral surface; and
   the step of depositing comprises depositing the absorbent particulate polymer material from the first plurality of reservoirs onto the first substrate disposed on the first grid while the first support and first printing roll are arranged such that the machine direction of the first grid is substantially parallel to the machine direction of the first peripheral surface and the cross direction of the first grid is substantially parallel to the cross direction of the first peripheral surface.

3. The method of claim 2 wherein:
   the second grid of the second support extends in a machine direction and a cross direction substantially perpendicular to the machine direction and the second plurality of cross bars extend in the cross direction of the second grid and spaced from one another so that the channels extend between the second plurality of cross bars in the cross direction of the second grid;
   the peripheral surface of the second printing roll extends in a machine direction and a cross direction substantially perpendicular to the machine direction, the rows of second plurality of reservoirs extend in the cross direction of the second peripheral surface and are spaced from one another in the machine direction of the second peripheral surface;

and the step of depositing the absorbent particulate polymer material from the second plurality of reservoirs comprises depositing the absorbent particulate polymer material from the second plurality of reservoirs onto the second substrate disposed on the second grid while the second support and second printing roll are arranged such that the machine direction of the second grid is substantially parallel to the machine direction of the second peripheral surface and the cross direction of the second grid is substantially parallel to the cross direction of the second peripheral surface.

4. The method of claim 1, wherein the rows of absorbent particulate polymer material on the first substrate are separated by junction areas between the rows of absorbent particulate polymer material.

5. The method of claim 1, wherein the rows of absorbent particulate polymer material on the first and second substrates are separated by junction areas between the rows of absorbent particulate polymer material and the step of combining comprises combining said first and second absorbent layers together so that the rows of absorbent particulate polymer material on the first substrate are disposed between and substantially parallel to rows of absorbent particulate polymer material on the second substrate.

6. The method of claim 1, wherein the step of combining the first and second absorbent layers comprises combining the first and second absorbent layers together such that the first and second patterns of absorbent particulate polymer material are offset from one another in the machine direction.

7. The method of claim 1, wherein:

the first support is a first support roll and the step of depositing the absorbent particulate polymer material on the first substrate further comprises depositing the absorbent particulate polymer material on the first substrate by rotating the first printing roll and rotating the first support roll; and the second support is a second support roll and the step of depositing the absorbent particulate polymer material on the second substrate further comprises depositing the absorbent particulate polymer material on the second substrate by rotating the second printing roll and rotating the second support roll.

8. The method of claim 7, wherein:

the first support roll is a first vacuum support roll and the step of depositing the absorbent particulate polymer material on the first substrate further comprises holding the first substrate to the first vacuum support roll with a vacuum; and the second support roll is a second vacuum support roll and the step of depositing the absorbent particulate polymer material on the second substrate further comprises holding the second substrate to the second vacuum support roll with a vacuum.

9. The method of claim 1, wherein the first and second plurality of reservoirs are cylindrical or conical.

10. The method of claim 9, wherein the plurality of reservoirs in the second printing roll have a diameter of about 3 to about 8 mm, a spacing in a cross direction of about 5.5 to about 10 mm from reservoir center to reservoir center, and a spacing in a machine direction of about 8 to about 10 mm from reservoir center to reservoir center.

11. The method of claim 1, wherein the first substrate is disposed on the first grid so that the first substrate directly contacts at least some of the first plurality of cross bars.

12. The method of claim 1, wherein the first grid further comprises a plurality of spacers spaced from one another and extending between the first plurality of cross bars in the machine direction of the first support.

\* \* \* \* \*